United States Patent [19]
Martin et al.

[11] Patent Number: 5,976,503
[45] Date of Patent: *Nov. 2, 1999

[54] DISPOSABLE PLUG-IN AIR FRESHENER WITH HEAT ACTIVATED CARTRIDGE

[75] Inventors: John Martin, Caledonia; Mark E. Wefler, Mount Pleasant, both of Wis.

[73] Assignee: S. C. Johnson & Son, Inc., Racine, Wis.

[ * ] Notice: This patent is subject to a terminal disclaimer.

[21] Appl. No.: 08/834,070

[22] Filed: Apr. 14, 1997

[51] Int. Cl.$^6$ .................................................. A61L 9/04
[52] U.S. Cl. ........................... 424/43; 424/45; 424/76.1; 424/76.2; 424/76.3
[58] Field of Search ............... 424/43, 45, 76.1, 424/76.2, 76.3

[56] References Cited

U.S. PATENT DOCUMENTS

| | | | |
|---|---|---|---|
| 1,994,932 | 3/1935 | Vidal | 99/18 |
| 2,597,195 | 5/1952 | Smith | 21/119 |
| 2,802,695 | 8/1957 | Johnson | 299/24 |
| 2,804,291 | 8/1957 | Hard af Segerstad | 261/99 |
| 3,067,310 | 12/1962 | Walz et al. | 219/19 |
| 3,266,661 | 8/1966 | Dates | 220/64 |
| 3,288,556 | 11/1966 | Weber | 21/120 |
| 3,431,393 | 3/1969 | Katsuda | 219/274 |
| 3,482,929 | 12/1969 | Gentil | 21/53 |
| 3,550,853 | 12/1970 | Gray | 239/44 |
| 3,633,881 | 1/1972 | Yurdin | 261/24 |
| 4,020,321 | 4/1977 | Oswald | 209/271 |
| 4,037,352 | 7/1977 | Hennart et al. | 43/129 |
| 4,228,124 | 10/1980 | Kashihara et al. | 422/36 |
| 4,286,754 | 9/1981 | Jones | 239/6 |
| 4,314,915 | 2/1982 | Wiegers et al. | 252/522 |
| 4,411,829 | 10/1983 | Schulte-Elte et al. | 252/522 |
| 4,413,779 | 11/1983 | Santini | 239/45 |
| 4,434,306 | 2/1984 | Kobayashi et al. | 568/820 |
| 4,454,987 | 6/1984 | Mitchell | 239/6 |
| 4,849,255 | 7/1989 | Grise et al. | 427/122 |
| 4,849,606 | 7/1989 | Martens, III et al. | 219/271 |
| 4,857,384 | 8/1989 | Mio et al. | 428/164 |
| 4,912,306 | 3/1990 | Grise et al. | 219/549 |
| 4,913,350 | 4/1990 | Purzycki | 239/44 |
| 4,935,156 | 6/1990 | van Konynenburg et al. | 219/553 |
| 4,968,487 | 11/1990 | Yamamoto et al. | 422/125 |
| 5,000,383 | 3/1991 | van der Heijden | 239/47 |
| 5,038,394 | 8/1991 | Hasegawa et al. | 392/395 |

(List continued on next page.)

FOREIGN PATENT DOCUMENTS

| | | |
|---|---|---|
| 0 689 766 | 1/1996 | European Pat. Off. . |
| 2 432 837 | 3/1980 | France . |
| 2 741 807 | 6/1997 | France . |
| 2741807 | 6/1997 | France . |
| 36 09 511 | 10/1986 | Germany . |
| 41 31 613 | 3/1993 | Germany . |
| 44 46 413 | 6/1996 | Germany . |
| 94/15650 | 7/1994 | WIPO . |
| 9415650 | 7/1994 | WIPO . |
| 2 275 608 | 9/1994 | WIPO . |

*Primary Examiner*—Jose' G. Dees
*Assistant Examiner*—Kathryne E. Shelborne

[57] ABSTRACT

This invention provides an air freshener dispenser device comprising (1) a disposable air freshener cartridge, and (2) a disposable electrical plug housing. The cartridge has an elongated thermoplastic hollow body configuration with a sealed internal reservoir chamber of liquid air freshener medium, and the upper section of the cartridge body is shaped to a flat shallow extension of the cartridge chamber. An electrical-resistance heating element is affixed on the inner surface of the cartridge chamber shallow extension. A thin wick matrix extends internally from the cartridge chamber bottom up to the top of the chamber shallow extension. The cartridge has an integrally structured means adapted for removal of a top portion of the cartridge chamber shallow extension to expose an upper section of wick matrix to the atmosphere. The electrical plug housing is detachably secured and positioned proximate to the cartridge heating element. Activation of the heating element promotes air freshener dispersion into the atmosphere from the exposed wick.

17 Claims, 2 Drawing Sheets

U.S. PATENT DOCUMENTS

| | | | |
|---|---|---|---|
| 5,106,540 | 4/1992 | Barma et al. | 252/511 |
| 5,234,162 | 8/1993 | Sullivan | 239/56 |
| 5,242,111 | 9/1993 | Nakoneczny et al. | 239/47 |
| 5,290,546 | 3/1994 | Hasegawa et al. | 424/76.2 |
| 5,364,027 | 11/1994 | Kuhn | 239/44 |
| 5,382,384 | 1/1995 | Baigrie et al. | 252/511 |
| 5,415,934 | 5/1995 | Mori | 428/408 |
| 5,574,821 | 11/1996 | Babasade | 392/392 | form
DISPOSABLE PLUG-IN AIR FRESHENER WITH HEAT ACTIVATED CARTRIDGE

BACKGROUND OF THE INVENTION

This invention generally relates to dispensers of vaporizable media. More specifically, this invention relates to a device for dispensing a fragrance or deodorant in the form of a vapor for air freshening in an enclosed environment.

The need for effectively combating airborne malodors in homes and enclosed public buildings, by odor masking or destruction, is well established. Various kinds of vapor-dispensing devices have been employed for this purpose. The most common of such devices is the aerosol container which propels minute droplets of an air freshener composition into the air. Another common type of dispensing device is a dish containing or supporting a body of gelatinous matter which when it dries and shrinks releases a vaporized air-treating composition into the atmosphere. Other products such as deodorant blocks are also used for dispensing air-treating vapors into the atmosphere by evaporation. Another group of vapor-dispensing devices utilizes a carrier material such as paperboard impregnated or coated with a vaporizable composition.

A number of recent developments include a liquid air-treating composition in an enclosure, all or part of which is formed of a polymeric film through which the air-treating composition can migrate to be released as a vapor at an outer surface. Use of this type of permeable polymeric membrane controls the dispensing of air-treating vapors and tends to eliminate great variations in the rate of dispensing over the life of the product.

Wicking devices are well known for dispensing volatile liquids into the atmosphere, such as fragrance, deodorant, disinfectant or insecticide active agent.

A typical wicking device utilizes a combination of a wick and emanating region to dispense a volatile liquid from a liquid reservoir. Wicking devices are described in U.S. Pat. Nos. 1,994,932; 2,597,195; 2,802,695; 2,804,291; 3,550,853; 4,286,754; 4,413,779; 4,454,987; 4,913,350; and 5,000,383; incorporated by reference. of wicking device is described in U.S. Pat. Nos. 3,288,556; 3,431,393; 3,482,929; 3,633,881; 4,020,321; 4,968,487; 5,038,394; 5,290,546; and 5,364,027; incorporated by reference.

Some air freshener dispensers are expensive to manufacture. Other air freshener dispensers are inexpensive to produce, but tend to have inferior construction and functionality.

There remains a need for a well-constructed air freshener dispenser device which can be mass-produced economically and which can deliver a vapor medium at a controlled uniform rate over an extended period of time.

Accordingly, it is an object of this invention to provide an improved air freshener dispenser device for delivering an odorant and/or deodorant vapor in an enclosed environment.

It is another object of this invention to provide an air freshener dispenser device with a primary structure which is a plastic assembly that can be produced economically by a thermoforming means.

It is another object of this invention to provide a disposable air freshener dispenser device which has an interactive combination of an electrical plug and an air freshener cartridge unit having an affixed heating element.

It is a further object of this invention to provide an air freshener cartridge for utility in a plug-in air freshener dispenser device, wherein the cartridge has an affixed heating element, and an internal air freshener reservoir in contact with a wicking means.

Other objects and advantages of the present invention shall become apparent from the accompanying description and drawings.

SUMMARY OF THE INVENTION

One or more objects of the present invention are accomplished by the provision of a disposable air freshener dispenser device which is adapted for engagement and support by an electrical outlet, and which is an assembly of structural units comprising:

(1) a disposable cartridge having (a) an elongated thermoplastic hollow body configuration with a sealed internal reservoir chamber of liquid air freshener medium, and the upper section of the cartridge body is shaped to a flat shallow extension of the cartridge chamber;

(b) a thin wick matrix which extends internally from the cartridge chamber bottom up to the top of the chamber shallow extension;

(c) integrally structured means adapted for removal of a top portion of the cartridge chamber shallow extension to expose an upper section of wick matrix to the atmosphere; and (d) an electrical-resistance heating element means which is affixed to the inner surface of the said cartridge chamber shallow extension, and which is integrated with two vertical slots adjacent to the sides of the cartridge chamber shallow extension; and (2) an electrical plug housing which is detachably secured and positioned proximate to the heating element affixed to the inner surface of the cartridge chamber shallow extension, wherein the electrical plug housing has two metal prongs which are positioned within the cartridge vertical slots, and which extend rearwardly from the cartridge for engagement with an electrical outlet and for conduction of an electric current to the said heating element, whereby air freshener wicking into the atmosphere is heat-promoted.

In another embodiment this invention provides a disposable air freshener cartridge which is adapted for utility as a module in a heat-activated air freshener device, wherein the cartridge structure comprises:

(a) an elongated thermoplastic hollow body configuration with a sealed internal reservoir chamber of liquid air freshener medium, and the upper section of the cartridge body is sloped to a flat shallow extension of the cartridge chamber;

(b) a thin wick matrix which extends internally from the cartridge chamber bottom up to the top of the chamber shallow extension;

(c) integrally structured means adapted for removal of a top portion of the cartridge chamber shallow extension to expose an upper section of the wick matrix to the atmosphere; and (d) an electrical-resistance heating element means which is affixed to the inner surface of the said cartridge chamber shallow extension, and which is adapted to integrate with an electrical plug housing for heat generation.

DESCRIPTION OF THE DRAWINGS

FIG. 2 illustrates a rear thermoplastic section before and after juxtapositioning and sealing on a front thermoplastic section.

DESCRIPTION OF THE PREFERRED EMBODIMENTS

Figure 1:
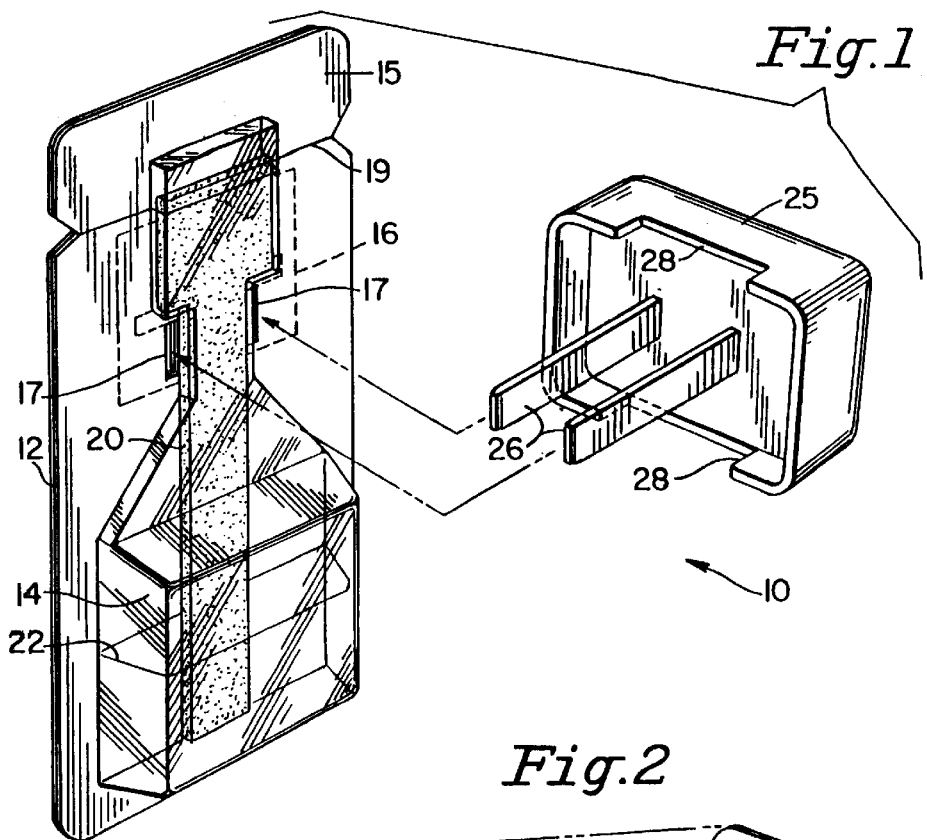
FIG. 1 is a composite perspective view of an invention air freshener dispenser device.

FIG. 1 illustrates an exploded view of present invention air freshener dispenser device 10 which consists of a disposable electrical plug and a disposable air freshener cartridge.

In assembled form, metal prongs 26 of disposable electrical plug housing 25 are inserted through vertical slots 17 of disposable cartridge 12, and plugged into a wall electrical outlet. Cartridge 12 is secured in a vertical position by electrical plug housing 25. Recesses 28 of electrical plug housing 25 are adapted to accommodate the structural configuration of the shallow extension of reservoir chamber 14 of disposable cartridge 12.

Electrical plug housing 25 typically is a plastic structure formed by molding means from a thermoset polymer such as phenol-formaldehyde resin, epoxy resin, polyphenylene sulfide, polyphenylene oxide, polycarbonate, polyimide, polybenzimidazole, and the like, or a thermoplastic polymer such as polyethylene, polypropylene, polyamide, and the like. For ease of construction and economy, electrical plug housing 25 and prongs 26 can comprise a unitary structure which is molded from a thermoset or thermoplastic polymer, and the surfaces of prongs 26 are metallized for conduction of electric current from an electrical outlet.

When air freshener dispenser device 10 is operational, electrical plug housing 25 encompassing the shallow extension of reservoir chamber 14, and heating element 16 which is affixed to the inner surface of the shallow extension of reservoir chamber 14, and additionally wick matrix 20 which is positioned within reservoir chamber 14 and its shallow extension. Electrical plug housing 25 insulates and contains the heat generated by heating element 16, and additionally functions as a child-proof shield.

Figure 2:
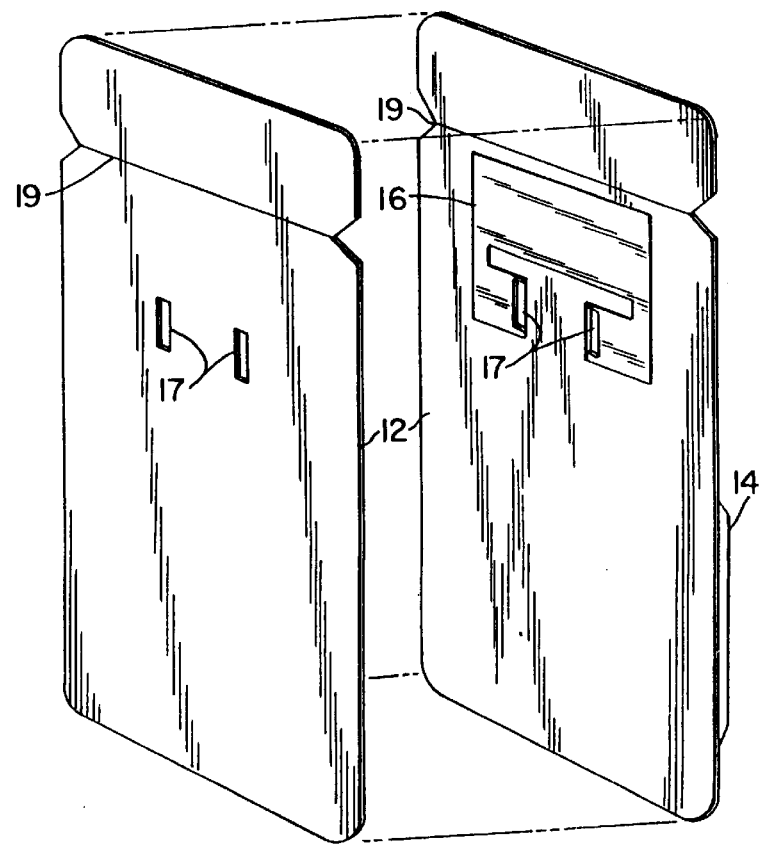
FIG. 2 is a composite perspective rear view of a disposable air freshener cartridge of an invention air freshener dispenser device.

A novel aspect of air freshener dispenser device 10 in FIG. 1 is the structural design of disposable cartridge 12. As illustrated in FIG. 2, cartridge 12 is a construction of sealed juxtapositioned sections of molded vapor-impermeable polyvinyl thin film having transparency. Typically cartridge 12 is a translucent or transparent structure which is injection or thermoform molded from a polymer such as polyethylene, polypropylene, polystyrene, polyvinyl chloride, polyvinyl acetate, polyamide, polyacrylamide, polymethacrylate, and the like.

Cartridge 12 of air freshener dispenser device 10 as illustrated in FIG. 1 and FIG. 2 typically has rectangular periphery dimensions between about 1–3 inches in width and 2–6 inches in length.

Hollow body 14 of disposable cartridge 12 in FIG. 1 has a sealed internal reservoir chamber with a content of liquid or gel air freshener medium 22.

Top portion 15 of cartridge 12 is adapted for removal by manual flexing or twisting along detaclunent line 19, whereby the upper section of internal wick matrix 20 is exposed to the atmosphere.

Internally-affixed electrical-resistance element 16 in FIG. 1 and FIG. 2 can be in the form of a printed electric-conductive ink or electric-conductive polymer coating with electrical-resistance properties for heat generation. Printed or thin film electrical-resistance heating elements are described in publications such as U.S. Pat. Nos. 3,067,310; 3,266,661; 4,849,255; 4,857,384; 4,912,306; 4,935,156; 5,106,540; 5,382,384; and 5,415,934; incorporated by reference.

Figure 3:
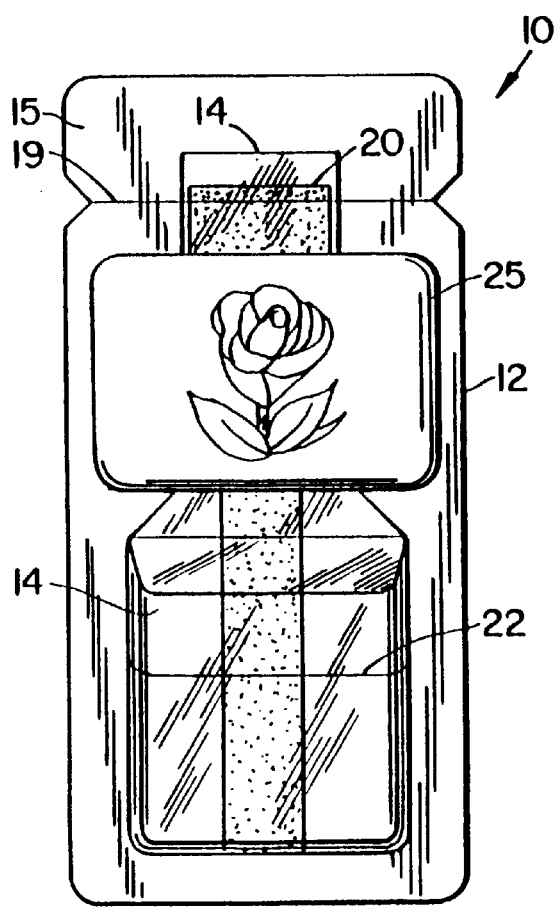
FIG. 3 is an elevational front view of a FIG. 1 invention air freshener dispenser device in assembled form.
Figure 4:
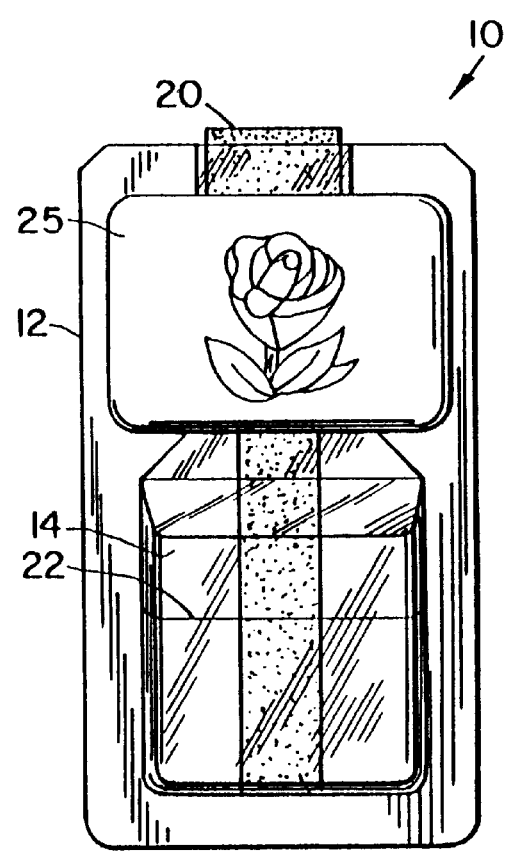
FIG. 4 is an elevational front view of a FIG. 3 invention air freshener dispenser device with an internal wick structure exposed to the environment.

When air freshener dispenser device 10 is in assembled form as illustrated in FIG. 3, and is in engagement with a wall electrical outlet, heating element 16 (as represented in FIG. 1 and FIG. 2) together with metal prongs 26 in plug housing 25 establish an electric circuit. When plug housing 25 draws electric current from an electrical outlet, heating element 16 functions as a heat source and promotes the dispersion of air freshener medium 22 as a vapor into the atmosphere from exposed wick matrix 20 in cartridge 12 (as represented in FIG. 4).

Wick matrix 20 extends from the top of hollow body 14 to the lower area, where wick matrix 20 is immersed in air freshener medium 22.

Wick matrix 20 can be an organic or inorganic liquid-permeable structure, such as a porous thermoplastic, thermoset, cellulosic or ceramic composition. Wick matrix 20 also can be in the form of a fibrous aggregate or a grooved nonporous strip. A variety of wick compositions and structures suitable for air freshener dispenser devices are described in U.S. Pat. Nos. 3,431,393; 3,482,929; 3,633,881; 4,020,321; 4,968,487; 5,038,394; and 5,290,546; incorporated by reference.

Air freshener medium 22 in FIGS. 1–4 can be any air treating material which is transported upward through wick matrix 20 by capillary action, and dispersed into the atmosphere in vapor form. Typically air freshener medium 22 is a fragrance or a deodorant formulation in liquid form.

Air freshener medium 22 preferably is a liquid fragrance comprising one or more volatile organic compounds which are available from perfumery suppliers such as Firmenich Inc., Takasago Inc., Noville Inc., Quest Co., and Givaudan-Roure Corp.

Most conventional fragrance materials are volatile essential oils. The fragrance can be a synthetically formed material, or a naturally derived oil such as oil of Bergamot, Bitter Orange, Lemon, Mandarin, Caraway, Cedar Leaf, Clove Leaf, Cedar Wood, Geranium, Lavender, Orange, Origanum, Petitgrain, White Cedar, Patchouli, Lavandin, Neroli, Rose absolute, and the like.

A wide variety of chemicals are known for perfumery, such as aldehydes, ketones, esters, alcohols, terpenes, and the like. A fragrance can be relatively simple in composition, or can be a complex mixture of natural and synthetic chemical components.

A typical scented oil can comprise woody/earthy bases containing exotic constituents such as sandalwood oil, civet, patchouli oil, and the like. A scented oil can have a light floral fragrance, such as rose extract or violet extract. Scented oil also can be formulated to provide desirable fruity odors, such as lime, lemon or orange.

Synthetic types of fragrance compositions either alone or in combination with natural oils are described in U.S. Pat. Nos. 4,314,915; 4,411,829; and 4,434,306; incorporated herein by reference. Other artificial liquid fragrances include geraniol, geranyl acetate, eugenol, isoeugenol, linalool, linalyl acetate, phenethyl alcohol, methyl ethyl ketone, methylionone, isobornyl acetate, and the like.

Air freshener medium 22 also can be a liquid formulation containing a volatile pesticide such as p-dichlorobenzene, or a therapeutic agent such as menthol.

Disposable cartridge 12 in FIGS. 1–4 preferably is constructed of transparent or translucent materials, such that air freshener medium 22 is visible during usage for an indication of the liquid level in the interior reservoir of cartridge 12.

FIG. 3 is an elevational front view of FIG. 1 air freshener dispenser device 10 in assembled form. The front surface of electrical plug housing 25 can be printed with a logo or artistic design.

FIG. 4 is an elevational front view of air freshener dispenser device 10 in FIG. 3, which illustrates the removal of top portion 15 of cartridge 12, and the exposure of the upper section of wick matrix 20 to the atmosphere. When air freshener dispenser device 10 is operational, internal heating element 16 promotes transport of air freshener medium 22 up wick matrix 20, and dispersion into the atmosphere as a vapor.

A significant advantage derives from the incorporation of heating element 16 in the structure of disposable cartridge 12. A different heating element 16 can be designed for different air freshener medium 22 formulations. The combination of heating element 16 and specific air freshener medium 22 can be customized for optimum performance.

As a further advantage, a present invention air freshener dispenser device can be produced in high volume from relatively inexpensive materials. After usage, the device qualifies for disposal as a non-hazardous solid waste.

What is claimed is:

1. An air freshener dispenser device which is adapted for engagement and support by an electrical outlet, and which is an assembly of structural units, the dispenser device comprising:

a disposable cartridge having (a) an elongated thermoplastic hollow body with a sealed internal reservoir chamber of liquid air freshener medium and an extension extending up from and contiguous with the cartridge chamber, the body having two vertical slots extending therethrough, the slots being disposed on either side of the extension; (b) a wick matrix comprising a lower section disposed in the cartridge chamber and an upper section extending into the chamber extension; (c) integrally structured means for facilitating removal of a top portion of the chamber extension to expose the upper section of the wick matrix to the atmosphere; and (d) an electrical-resistance heating element affixed to the cartridge body adjacent to the chamber extension for heating the wick matrix and integrated with the two vertical slots; and an electrical plug housing which is detachably securable to the cartridge proximate to the heating element, the electrical plug housing comprising two metal prongs which are insertable through the cartridge vertical slots, so as to engage the heating element and extend rearwardly from the cartridge for engagement with the electrical outlet to conduct electric current to the heating element, whereby air freshener wicking into the atmosphere is heat-promoted.

2. A dispenser device in accordance with claim 1, wherein the hollow body of the cartridge is a construction of sealed, juxtapositioned sections of molded, vapor-impermeable polyvinyl thin film having transparency so that the air freshener medium in the reservoir chamber is visible.

3. A dispenser device in accordance with claim 1, wherein the wick matrix is a porous structure selected from the group consisting of thermoplastic, cellulosic and ceramic compositions.

4. A dispenser device in accordance with claim 1, wherein the air freshener medium is a liquid fragrance composition.

5. A dispenser device in accordance with claim 1, wherein the air freshener medium is a liquid pesticide composition.

6. A dispenser device in accordance with claim 1, wherein the air freshener medium is a liquid therapeutic composition.

7. A dispenser device in accordance with claim 1, wherein the electrical-resistance heating element is one of a film coating and a printed pattern.

8. A dispenser device in accordance with claim 1, wherein the electrical plug housing and two prongs are a unitary structure molded from a polymer selected from the group consisting of thermoplastics and thermosets and the prongs have metallized surfaces to conduct electric current.

9. A dispenser device in accordance with claim 1, wherein the electrical plug housing encases the extension so as to insulate the extension and the heating element when the dispenser device is operational, and function as a child-proof shield.

10. A disposable air freshener cartridge which is adapted for use with an electrical plug housing in a heat-activated air freshener device, the cartridge comprising:

an elongated thermoplastic hollow body with a sealed internal reservoir chamber of liquid air freshener medium and an extension extending up from and contiguous with the cartridge chamber;

a wick matrix comprising a lower section disposed in the cartridge chamber and an upper section extending into the chamber extension;

integrally structured means for facilitating removal of a top portion of the chamber extension to expose the upper section of the wick matrix to the atmosphere; and an electrical-resistance heating element affixed to the cartridge body adjacent to the chamber extension for heating the wick matrix, and which is adapted to integrate with the electrical plug housing for heat generation.

11. A vaporizable liquid medium dispenser device which is adapted to be plugged into an electrical outlet, the dispenser device comprising:

a disposable cartridge comprising (a) an elongated, hollow thermoplastic body comprising a bottom portion, having two vertical slots extending therethrough, and a top portion detachable from the bottom portion, the body including a sealed internal chamber, the chamber including (i) a reservoir disposed in the bottom portion of the body and containing liquid medium and (ii) an extension extending from the reservoir to the top portion of the body; (b) a wick matrix disposed within the chamber and extending from the liquid in the reservoir up to the extension so that detachment of the top portion of the body exposes an upper section of the wick matrix to the atmosphere; and (c) an electrical-resistance heating element affixed to the bottom portion of the body in thermal communication with the extension of the chamber for heating the wick matrix, and which is adjacent to the two vertical slots of the body; and an electrical plug housing which is detachably securable to the cartridge and includes two metal prongs which fit within the two vertical slots of the body, so as to engage the heating element and extend rearwardly from the cartridge for insertion into the electrical outlet, so as to conduct electric current to the heating element.

12. The dispenser device according to claim 11, wherein the thermoplastic body of the cartridge comprises a plurality of molded, vapor impermeable polyvinyl thin film layers sealed together, at least one of the layers having transparency so that the liquid medium in the reservoir is visible.

13. The dispenser device according to claim 11, wherein the wick matrix is formed of a porous material selected from the group consisting of thermoplastics, cellulosic compositions, and ceramic compositions.

14. The dispenser device according to claim 11, wherein the liquid medium is selected from the group consisting of a fragrance, a pesticide, and a therapeutic agent.

15. The dispenser device according to claim 11, wherein the electrical resistance heating element comprises one of a film coating and a printed pattern.

16. The dispenser device according to claim 11, wherein the electrical plug housing and the two prongs are molded as a unitary structure from a polymer selected from the group consisting of thermoplastics and thermosets, and the prongs are metallized so as to be electrically conductive.

17. The dispenser device according to claim 11, wherein the electrical plug housing is securable to the cartridge so as to encase and insulate the extension and the heating element.

* * * * *